United States Patent
Keppler

(10) Patent No.: US 6,921,768 B2
(45) Date of Patent: Jul. 26, 2005

(54) CYTOSTATIC CERIUM COMPOUNDS

(75) Inventor: Bernhard Keppler, Hockenheim (DE)

(73) Assignee: Faustus Forschungs Cie. Translational Cancer Research GmbH, Leipzig (DE)

(*) Notice: Subject to any disclaimer, the term of this patent is extended or adjusted under 35 U.S.C. 154(b) by 0 days.

(21) Appl. No.: 10/773,928

(22) Filed: Feb. 6, 2004

(65) Prior Publication Data

US 2004/0223915 A1 Nov. 11, 2004

Related U.S. Application Data

(63) Continuation of application No. PCT/EP02/08766, filed on Aug. 6, 2002.

(30) Foreign Application Priority Data

Aug. 6, 2001 (DE) ............................. 101 38 561

(51) Int. Cl.$^7$ ................. A61K 31/444; A61K 31/4375; C07D 213/22; C07D 471/06
(52) U.S. Cl. .................... 514/285; 514/334; 546/88; 546/258
(58) Field of Search ................. 514/285, 334; 546/88, 258

(56) References Cited

PUBLICATIONS

F.A. Hart et al., "Lanthanide Complexes–III* Complexes Of 2,2'–Dipyridyl With Lanthanide Chlorides, Thiocyanates, Acetates And Nitrates", *J. Inorg. Nucl. Chem.*, vol. 27, pp. 1825–1829, (1965).

F.A. Hart et al., "Complexes Of 1,10'–Phenanthroline With Lanthanide Chlorides, Thiocyanates", *J. Inorg. Nucl. Chem.*, vol. 26, pp. 579–585, (1964).

*Primary Examiner*—Taofiq Solola
(74) *Attorney, Agent, or Firm*—Akin Gump Strauss Hauer & Feld, LLP

(57) ABSTRACT

The invention relates to cerium compounds having general formulas (I) $R_n^{i+}Y_i^{n-}$ and (II) $R_b^+Y_b^+$ and their application as medicaments in the prophylaxis and/or treatment of cancer diseases. In formula (I), R is a group of general formula (A):

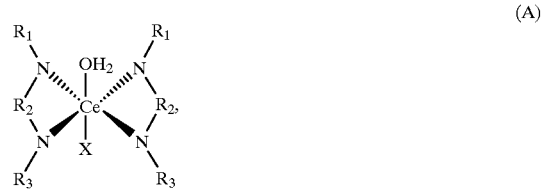

(A)

and in formula (II), $R_b$ is a group of general formula (B)

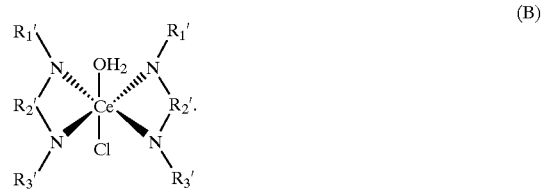

(B)

12 Claims, No Drawings

CYTOSTATIC CERIUM COMPOUNDS

CROSS-REFERENCE TO RELATED APPLICATIONS

This application is a continuation of International Application No. PCT/EP02/08766, filed Aug. 6, 2002 and the disclosure of which is incorporated herein by reference.

BACKGROUND OF THE INVENTION

This invention relates to cerium compounds and their use as medicaments for the prevention, prophylaxis and/or treatment of cancer diseases.

The object of this invention is to provide a compound which exhibits high effectiveness in the treatment of cancer diseases.

BRIEF SUMMARY OF THE INVENTION

This invention provides a compound of general formula (I)

(I), wherein R is a group of general formula (A):

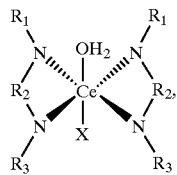
(A)

wherein $R_1$ and $R_3$ are independently selected from the substituted and unsubstituted group consisting of $C_1$–$C_{10}$-alkyl, $C_3$–$C_6$-cycloalkyl, $C_3$–$C_6$-cycloalkenyl, $C_2$–$C_{10}$-alkenyl, $C_6$–$C_{14}$-aryl and a heterocycle, and hydrogen;

$R_2$ is selected from the substituted and unsubstituted group consisting of $C_1$–$C_6$-alkylene, $C_3$–$C_6$-cycloalkylene, $C_3$–$C_6$-cycloalkenylene, $C_2$–$C_6$-alkenylene, $C_6$–$C_{14}$-arylene and a heterocycle;

$R_1$ and $R_2$ and/or $R_2$ and $R_3$ can form a heterocycle optionally containing further nitrogen atoms;

X is a halogen;

Y is a physiologically compatible anion;

i and n are independently natural numbers $\geq 1$, and physiologically compatible addition salts, provided that the compound of general formula (I) is not:

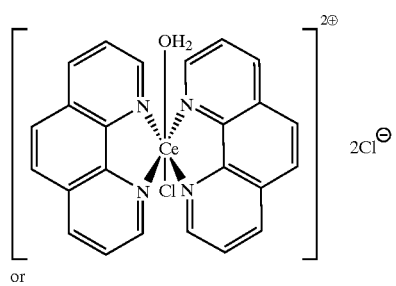

or

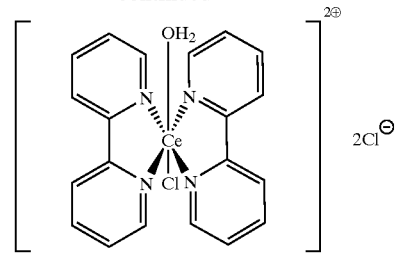

A medicament containing a compound of general formula (I) is also provided by the invention.

Further, the invention provides a compound of general formula (II)

(II), wherein $R_b$ is a group of general formula (B)

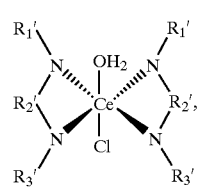
(B)

wherein $R_1'$ and $R_3'$ are independently selected from the substituted and unsubstituted group consisting of $C_1$–$C_{10}$-alkyl, $C_3$–$C_6$-cycloalkyl, $C_2$–$C_{10}$-alkenyl, $C_6$–$C_{14}$-aryl and a heterocycle and hydrogen;

$R_2'$ is selected from the substituted and unsubstituted group consisting of $C_1$–$C_6$-alkylene, $C_3$–$C_6$-cycloalkylene, $C_2$–$C_6$-alkenylene, $C_6$–$C_{14}$-arylene and a heterocycle;

$R_1'$ and $R_2'$ or $R_2'$ and $R_3'$ can form a heterocycle optionally including further nitrogen atoms; and $Y_b$ is selected from the group consisting of a metal halogen, a halogen, a pseudohalogen, $HCO_3$ and $R'COO$, where $R'$ is selected from the substituted and unsubstituted group consisting of $C_1$–$C_6$-alkyl, $C_2$–$C_6$-alkenyl and aryl.

DETAILED DESCRIPTION OF THE INVENTION

More specifically, the object of the invention is solved by a compound of the general formula (I)

(I), wherein R is a group of the general formula (A)

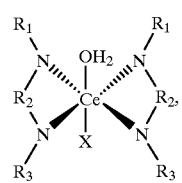
(A)

wherein $R_1$ and $R_3$ are independently selected from the group consisting of $C_1$–$C_{10}$-alkyl, $C_3$–$C_6$-cycloalkyl, $C_3$–$C_6$-cycloalkenyl, $C_2$–$C_{10}$-alkenyl, $C_6$–$C_{14}$-aryl and a heterocycle, which can in each case be substituted or unsubstituted, and hydrogen;

$R_2$ is selected from the group consisting of $C_1$–$C_6$-alkylene, $C_3$–$C_6$-cycloalkylene, $C_3$–$C_6$-cycloalkenylene, $C_2$–$C_6$-alkenylene, $C_6$–$C_{14}$-arylene and a heterocycle, which can in each case be substituted or unsubstituted;

and $R_1$ and $R_2$ and/or $R_2$ and $R_3$ can form a heterocycle which, optionally where applicable, can contain other nitrogen atoms;

X is a halogen;

Y is a physiologically compatible anion;

i and n are independent of one another and are natural numbers $\geq 1$, and physiologically compatible addition salts, provided that the compound of general formula (I) is not:

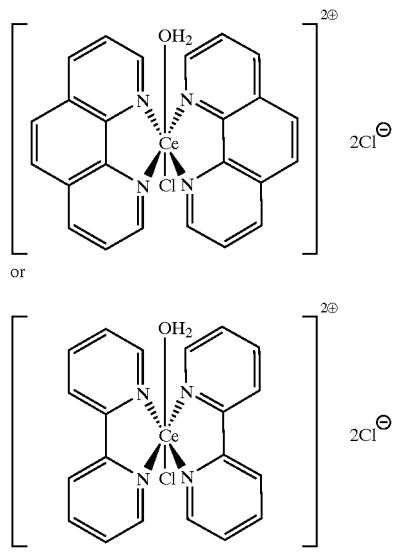

or

In a preferred embodiment $R_1$ and/or $R_3$ are $C_1$–$C_5$-alkyl, in particular methyl, ethyl or propyl. Also, $R_1$ and/or $R_3$ are preferably cyclobutyl, cyclopropyl, cyclobutenyl or cyclopropenyl and in particular cyclopentyl, cyclohexyl, cyclopentenyl or cyclohexenyl or $C_2$–$C_5$-alkenyl, in particular ethenyl, propenyl or butenyl. Furthermore, $R_1$ and/or $R_3$ can be benzyl or pyridyl.

$R_2$ is preferably $C_1$–$C_5$-alkylene, in particular methylene, ethylene or propylene. Also, $R_2$ is preferably cyclobutylene, cyclopropylene, cyclopentylene, cyclohexylene, cyclopentenylene or cyclohexenylene or $C_2$–$C_5$-alkenylene, in particular ethenylene, propenylene or butenylene. Furthermore $R_2$ can be benzylene or pyridylene.

$R_1$, $R_2$ and/or $R_3$ can be substituted by hydroxyl, amino, —$SO_3H$, halogen, $C_1$–$C_4$-alkyl, $C_2$–$C_4$-alkenyl, $C_3$–$C_6$-cycloalkyl, $C_3$–$C_6$-cycloalkenyl, $C_1$–$C_6$-aryl, $C_1$–$C_4$-alkoxy, $C_1$–$C_4$-alkoxy-$C_1$–$C_4$-alkylene, $C_1$–$C_4$-alkylmercapto, $C_1$–$C_4$-alkylmercapto-$C_1$–$C_4$-alkylene, formyl, carboxyl, $C_1$–$C_4$-alkoxycarbonyl, $C_1$–$C_4$-alkoxycarbonyl-$C_1$–$C_4$-alkylene, di-$C_1$–$C_4$-alkylamino, di-$C_1$–$C_4$-alkylamino-$C_1$–$C_4$-alkylene, di-$C_1$–$C_4$-alkylaminocarbonyl, di-$C_1$–$C_4$-alkylaminocarbonyl -$C_1$–$C_4$-alkylene, preferably halogen and especially methyl, ethyl or propyl, in particular if $R_1$ and $R_2$, and/or $R_2$ and $R_3$ form a heterocycle.

In a further preferred embodiment "i" is the number 2 and/or "n" is the number 1.

Also, X is preferably chlorine.

Furthermore, in the general formula (I), Y is preferably a metal halogen, a halogen, a pseudohalogen, $HCO_3$ or R'COO, where R' is $C_1$–$C_6$-alkyl, $C_2$–$C_6$-alkenyl or aryl, which in each case can be substituted or unsubstituted. In particular Y is Cl.

Organic or inorganic addition salts can be formed with the following anions: chloride, bromide, phosphate, carbonate, nitrate, perchlorate, sulphate, citrate, lactate, tartrate, maleate, fumarate, mandelate, benzoate, ascorbate, cinnamate, glycollate, methanesulphonate, formiate, malonate, naphthaline-2-sulphonate, salicylate and/or acetate.

As possible cations $H^+$, sodium and/or potassium cations can be used.

Furthermore, the object of this invention is solved by a medicament containing a compound of the general formula (I)

$$R_n^{i+}Y_i^{n-} \qquad (I),$$

where R is a group of the general formula (A)

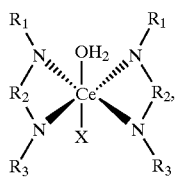
(A)

where $R_1$ and $R_3$ are independently selected from the group consisting of $C_1$–$C_{10}$-alkyl, $C_3$–$C_6$-cycloalkyl, $C_3$–$C_6$-cycloalkenyl, $C_2$–$C_{10}$-alkenyl, $C_6$–$C_{14}$-aryl and a heterocycle, which can in each case be substituted or unsubstituted, and hydrogen;

$R_2$ is selected from the group consisting of $C_1$–$C_6$-alkylene, $C_3$–$C_6$-cycloalkylene, $C_3$–$C_6$-cycloalkenylene, $C_2$–$C_6$-alkenylene, $C_6$–$C_{14}$-arylene and a heterocycle, which can in each case be substituted or unsubstituted;

and $R_1$ and $R_2$ and/or $R_2$ and $R_3$ can form a heterocycle which optionally, where applicable, can contain further nitrogen atoms;

X is a halogen;

Y is a physiologically compatible anion;

i and n are independent of one another and are natural numbers $\geq 1$, and physiologically compatible addition salts.

For the medicament, containing a compound of the general formula (I), with regard to the groups $R_1$, $R_2$, $R_3$, X, Y, i and n, the same embodiments are preferred as presented above for the compound according to the invention.

In the preferred embodiments the group R of the general formula (A) can be selected from:

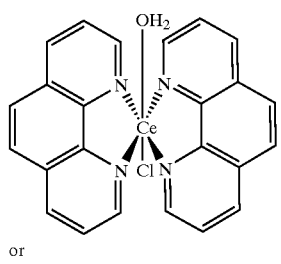

or

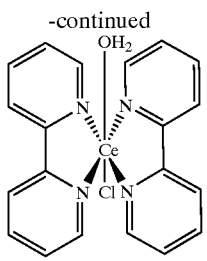

The compound according to the invention can be used for the prophylaxis and/or treatment of cancer diseases.

In another embodiment the object is solved by a compound of the general formula (II)

$$R_b^+ Y_b^- \tag{II}$$

where $R_b$ is a group of the general formula (B)

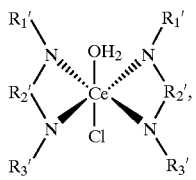

(B)

where $R_1'$ and $R_3'$ are independently selected from the group consisting of $C_1$–$C_{10}$-alkyl, $C_3$–$C_6$-cycloalkyl, $C_2$–$C_{10}$-alkenyl, $C_6$–$C_{14}$-aryl and a heterocycle, which can in each case be substituted or unsubstituted, and hydrogen.

$R_2'$ is selected from the group consisting of $C_1$–$C_6$-alkylene, $C_3$–$C_6$-cycloalkylene, $C_2$–$C_6$-alkenylene, $C_6$–$C_{14}$-arylene and a heterocycle, which in each case can be substituted or unsubstituted;

and $R_1'$ and $R_2'$ or $R_2'$ and $R_3'$ can form a heterocycle which can, optionally, where applicable, contain further nitrogen atoms;

and $Y_b$ is a metal halogen, a halogen, a pseudohalogen, $HCO_3$ or R'COO, where R' is $C_1$–$C_6$-alkyl, $C_2$–$C_6$-alkenyl or aryl, which in each case can be substituted or unsubstituted.

In preferred embodiments the group $R_b$ of the general formula (B) can be selected from:

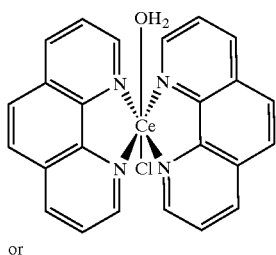

or

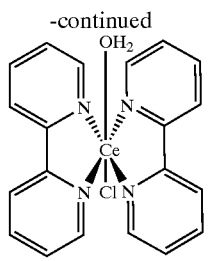

$R_1'$ and $R_3'$ are preferably $C_1C_5$-alkyl, especially methyl, ethyl, or propyl. Also, $R_1'$ and $R_3'$ are preferably cyclobutyl, cyclopropyl or $C_2$–$C_5$-alkenyl, in particular ethenyl, propenyl or butenyl. Furthermore, $R_1'$ and $R_3'$ can be benzyl or pyridyl.

$R_1'$ and $R_3'$ can also be substituted by methyl, ethyl or propyl, in particular when $R_1'$ and $R_2'$ or $R_2'$ and $R_3'$ form a heterocycle.

$R_2'$ is preferably $C_1$–$C_5$-alkylene, in particular methylene, ethylene or propylene. Also, $R_1'$ and $R_3'$ are preferably cyclobutylene, cyclopropylene, or $C_2$–$C_5$-alkenylene, in particular ethenylene, propenylene or butenylene. Furthermore $R_2'$ can be benzylene or pyridylene.

$R_2'$ can be substituted by methyl, ethyl or propyl, in particular when $R_1'$ and $R_2'$ or $R_2'$ and $R_3'$ form a heterocycle.

Furthermore, $Y_b$ in the general formula (II) is preferably Cl.

Also, the object of this invention is solved by a medicament which contains the compound according to the invention. The compound according to the invention can be used for the prevention, prophylaxis and/or treatment of cancer diseases.

In the following the medicament containing the compound according to the invention is described in more detail.

The medicament according to the invention is primarily administered intravenously, but also intramuscularly, intraperitoneally, subcutaneously or perorally. External application is also possible. Preferably, it is administered by intravenous injection or by intravenous infusion.

The medicament is manufactured according to known methods, whereby the compound according to the invention is used as such or, where applicable, in combination with suitable pharmaceutical carrier substances. If the medicament according to the invention contains pharmaceutical carrier substances as well as the active substance, the content of active substance in this mixture is about 0.1 to 99.5, preferably about 0.5 to 95% by weight of the total mixture.

The medicament according to the invention can be applied in any suitable formulation with the prerequisite that the establishment and maintenance of a sufficient level of active substance is ensured. This can, for example, be achieved by the oral or parenteral administration in suitable doses. Advantageously, the pharmaceutical preparation of the active substance is provided in the form of standard doses which are matched to the desired administration. A standard dose can, for example, be a tablet, dragée, capsule, suppository or a measured volume of a powder, granulate, solution, emulsion or suspension.

A "standard dose" for the purposes of this invention is taken to mean a physically determined unit which contains an individual quantity of the active constituent in combination with a pharmaceutical carrier substance and its content of active substance corresponds to a fraction or multiple of a therapeutic single dose. A single dose preferably contains the quantity of active substance which is administered during an application and which normally corresponds to a whole, half, third or quarter of the daily dose. If only a fraction, such as half or quarter of the standard dose is needed for a single therapeutically administered dose, then the standard dose is advantageously divisible, e.g. in the form of a tablet with a dividing groove.

The medicaments according to the invention can, if they are available in standard doses and intended for application, e.g. on persons, contain about 0.1 to 500 mg, preferably about 10 to 200 mg and particularly about 50 to 150 mg of active substance.

Generally in human medicine, the active substance(s) are administered in a daily dose of about 0.1 to 5, preferably about 1 to 3 mg/kg of body weight, where necessary in the form of a number, preferably about 1 to 3, of single intakes for achieving the desired results. A single intake contains the active substance(s) in quantities of about 0.1 to 5, preferably about 1 to 3 mg/kg of body weight. With oral treatment similar dosages can be applied.

The therapeutic administration of the medicament according to the invention can occur about 1 to 4 times daily at specified or varying time points, e.g. in each case before meals and/or in the evening. However, it may be necessary to deviate from the quoted dosages depending on the type, body weight and age of the individual to be treated, the type and severity of the disease, the type of preparation and the application of the medicament as well as the time period or interval within which the administration occurs. Consequently, in some cases it may be sufficient to use less than the amount of active substance mentioned above, whereas in other cases the above listed quantity of active substance must be exceeded. It may also be practicable to administer the medicaments only once or at intervals of a number of days.

The specification of the necessary optimum dosage and type of application of the active substances can be made by any specialist based on his specialist knowledge.

The medicaments according to the invention normally comprise the compounds according to the invention and non-toxic, pharmaceutically compatible medication carriers, which as additive or dilution agents, are employed, for example, in solid, semi-solid or liquid form or as a means of enclosure, for example in the form of a capsule, a tablet coating, a bag or another container for the therapeutically active constituent. A carrier material may, for example, act as an agent for the ingestion of the medicament by the body, as a formulation agent, sweetener, taste modifier, colorant or as a preservative.

For oral application, for example, tablets, dragées, hard and soft capsules, for example of gelatine, dispersible powder, granulate, aqueous and oily suspensions, emulsions, solutions and syrups can be employed.

Tablets can contain inert dilution agents, e.g. calcium carbonate, calcium phosphate, sodium phosphate or lactose; granulation and distributing agents, e.g. maize starch or alginate; binding agents, e.g. starch, gelatine or arabine; and lubricating agents, e.g. aluminium or magnesium stearate, talcum or silicone oil. They can also be provided with a coating which is produced such that it causes delayed release and resorption of the medicament in the gastro-intestinal tract, so that, for example, improved compatibility, assimilation or retardation is achieved. Gelatine capsules may contain the pharmaceutical substance mixed with a solid, e.g. calcium carbonate or kaolin or an oily dilution agent, e.g. olive, peanut or paraffin oil.

Aqueous suspensions can contain suspension agents, e.g. sodium carboxymethyl cellulose, methyl cellulose, hydroxypropyl cellulose, sodium alginate, polyvinyl pyrrolidon, traganth rubber or arabine; dispersant or wetting agents, e.g. polyoxyethylene stearate, heptadeca-ethylene-oxycatanol, polyoxyethylene sorbitol-monooleate, or lecithin; preservatives, e.g. methyl- or propylhydroxy-benzoate; taste modifiers; sweeteners, e.g. saccharose, lactose, sodium cyclamate, dextrose, invert sugar syrup.

Oily suspensions may be, for example, peanut, olive, sesame, coconut or paraffin oil and thickening agents, such as bees wax, high melting point wax or cetyl alcohol; also sweeteners, taste modifiers and antioxidants.

Powder and granulates dispersible in water may contain the compound according to the invention in a mixture with dispersing, wetting and suspension agents, e.g. those mentioned above as well as with sweeteners, taste modifiers and colorants.

Emulsions can, for example, contain olive, peanut or paraffin oil as well as emulsifying agents such as arabine, traganth rubber, phosphatides, sorbitan monooleate, polyoxyethylene sorbitan monooleate and sweeteners and taste modifiers.

Aqueous solutions can contain preservatives, e.g. methyl- or propylhydroxybenzoates; thickening agents; taste modifiers; sweeteners, e.g. saccharose, lactose, sodium cyclamate, dextrose, invert sugar syrup as well as taste modifiers and colorants.

For the parenteral application of the pharmaceutical substances sterile injectable aqueous solutions, isotonic salt solutions or other solutions can be used.

The invention will be further illustrated in accordance with the following non-limiting examples:

EXAMPLE 1

Synthesis of trans-[aquachlorobis(1,10-phenantrolin)cerium(III)]-dichloride

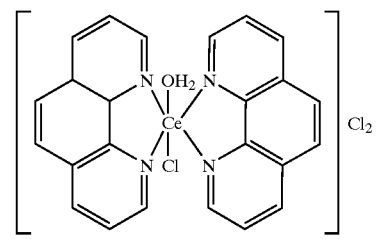

The manufacture of trans-[aquachlorobis(1,10-phenantrolin)cerium(III)]-dichloride (KP 776) was performed by adding cerium trichloride hexahydrate ($CeCl_3 \cdot 6H_2O$) as 0.05 M ethanolic solution to 1,10-phenantrolinmonohydrate as 0.16 M ethanolic solution in a molar ratio of 1:4. The precipitating product was filtered off after 24 hours, washed a number of times with ethanol and dried at room temperature in a vacuum.

EXAMPLE 2

Cytostatic activity of trans-[aquachlorobis(1,10-phenantrolin)cerium(III)]-dichloride First in vitro tests were carried out at the National Cancer Institute (Bethesda, Md., USA). In the 48-h sulphurhodamine B-assay on over 50 human tumour cell lines a good effectiveness was found with the following parameters:

| | | |
|---|---|---|
| Mean GI$_{50}$: | 0.98 μmol/l | 0.61 μg/ml |
| Mean TGI: | 15.1 μmol/l | 9.46 μg/ml |
| Mean LC$_{50}$: | 63.1 μmol/l | 39.4 μg/ml |

In this respect a certain selectivity for malignant melanoma was evident. Above average activities were also observed on single ovarian, kidney cell and parvicellular and non-parvicellular bronchial carcinoma cell lines.

In the propidium iodide assay on 13 human tumour xenografts and 10 human tumour cell lines a good cytostatic activity was also found with the following parameters:

| | | |
|---|---|---|
| Mean IC$_{50}$: | 1.92 μmol/l | 1.20 μg/ml |
| Mean IC$_{70}$: | 3.60 μmol/l | 2.25 μg/ml |
| Mean IC$_{90}$: | 11.6 μmol/l | 7.27 μg/ml |

Also here, the strongest effectiveness was found on a melanoma (xenograft).

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined b the appended claims.

I claim:

1. A compound of general formula (I)

$$R_n^{i+}Y_i^{n-} \quad (I),$$

wherein R is a group of general formula (A):

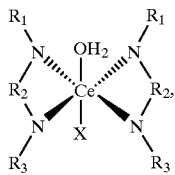

wherein

R$_1$ and R$_3$ are independently selected from the substituted and unsubstituted group consisting of C$_1$–C$_{10}$-alkyl, C$_3$–C$_6$-cycloalkyl, C$_3$–C$_6$-cycloalkenyl, C$_2$–C$_{10}$-alkenyl, C$_6$–C$_{14}$-aryl and a heterocycle, and hydrogen;

R$_2$ is selected from the substituted and unsubstituted group consisting of C$_1$–C$_6$-alkylene, C$_3$–C$_6$-cycloalkylene, C$_3$–C$_6$-cycloalkenylene, C$_2$–C$_6$-alkenylene, C$_6$–C$_{14}$-arylene and a heterocycle;

R$_1$ and R$_2$ and/or R$_2$ and R$_3$ can form a heterocycle optionally containing further nitrogen atoms;

X is a halogen;

Y is a physiologically compatible anion;

i and n are independently natural numbers ≧1, and physiologically compatible addition salts, provided that the compound of general formula (i) is not:

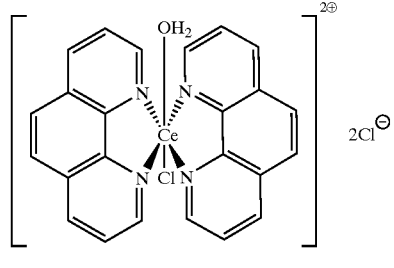

or

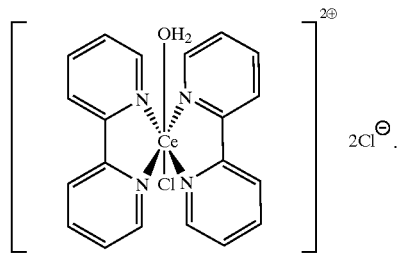

2. The compound according to claim 1, wherein Y in general formula (I) is Cl.

3. A medicament, containing a compound of general formula (I)

$$R_n^{i+}Y_i^{n-} \quad (I),$$

wherein R is a group of general formula (A)

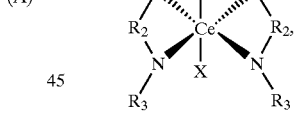

wherein

R$_1$ and R$_3$ are independently selected from the substituted and unsubstituted group consisting of C$_1$–C$_{10}$-alkyl, C$_3$–C$_6$-cycloalkyl, C$_3$–C$_6$-cycloalkenyl, C$_2$–C$_{10}$-alkenyl, C$_6$–C$_{14}$-aryl and a heterocycle, and hydrogen;

R$_2$ is selected from the substituted and unsubstituted group consisting of C$_1$–C$_6$-alkylene, C$_3$–C$_6$-cycloalkylene, C$_3$–C$_6$-cycloalkenylene, C$_2$–C$_6$-alkenylene, C$_6$–C$_{14}$-arylene and a heterocycle;

R$_1$ and R$_2$ and/or R$_2$ and R$_3$ can form a heterocycle optionally containing further nitrogen atoms;

X is a halogen;

Y is a physiologically compatible anion;

i and n are independently natural numbers ≧1, and physiologically compatible addition salts.

4. The medicament according to claim 3, wherein R of general formula (I) is:

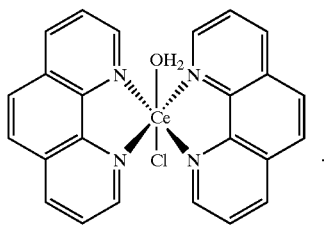

5. The medicament according to claim 3, wherein R of general formula (I) is:

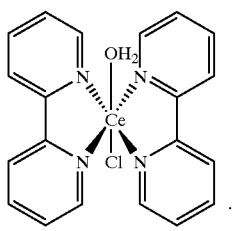

6. A method of treating cancer diseases comprising using a compound of general formula (I) according to claim 1.

7. A compound of general formula (II)

$$R_b^+ Y_b^+ \quad (II),$$

wherein $R_b$ is a group of general formula (B)

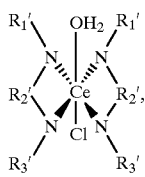

wherein $R_1'$ and $R_3'$ are independently selected from the substituted and unsubstituted group consisting of $C_1$–$C_{10}$-alkyl, $C_3$–$C_6$-cycloalkyl, $C_2$–$C_{10}$-alkenyl, $C_6$–$C_{14}$-aryl and a heterocycle, and hydrogen;

$R_2'$ is selected from the substituted and unsubstituted group consisting of $C_1$–$C_6$-alkylene, $C_3$–$C_6$-cycloalkylene, $C_2$–$C_6$-alkenylene, $C_6$–$C_{14}$-arylene and a heterocycle;

$R_1'$ and $R_2'$ or $R_2'$ and $R_3'$ can form a heterocycle optionally including further nitrogen atoms; and $Y_b$ is selected from the group consisting of a metal halogen, a halogen, a pseudohalogen, $HCO_3$ and R'COO, where R' is selected from the substituted and unsubstituted group consisting of $C_1$–$C_6$-alkyl, $C_2$–$C_6$-alkenyl and aryl.

8. The compound according to claim 7, wherein $R_b$ in general formula (B) is:

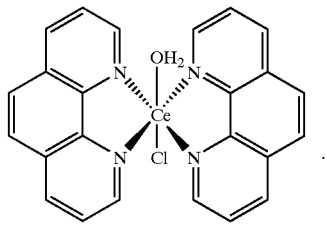

9. The compound according to claim 7, wherein $R_b$ in general formula (B) is:

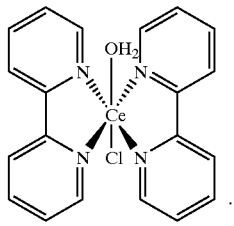

10. The compound according to claim 7, wherein $Y_b$ in general formula (II) is Cl.

11. A medicament containing a compound of general formula (II) according to claim 7.

12. A method of treating cancer diseases comprising applying a compound of general formula (II) according to claim 7.

* * * * *